(12) United States Patent
Kim

(10) Patent No.: US 6,648,891 B2
(45) Date of Patent: Nov. 18, 2003

(54) SYSTEM AND METHOD FOR FUSING SPINAL VERTEBRAE

(75) Inventor: Kee D. Kim, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 6 days.

(21) Appl. No.: 09/961,040

(22) Filed: Sep. 14, 2001

(65) Prior Publication Data

US 2003/0055430 A1 Mar. 20, 2003

(51) Int. Cl.[7] .......................... A61B 17/56; A61F 17/58
(52) U.S. Cl. .......................... 606/69; 606/102; 606/105
(58) Field of Search ............................. 606/60, 61, 69, 606/70, 72, 73, 74, 102, 105

(56) References Cited

U.S. PATENT DOCUMENTS

| | | | |
|---|---|---|---|
| 2,580,821 A | | 1/1952 | Nicola |
| 3,866,607 A | | 2/1975 | Forsythe et al. |
| 4,929,247 A | * | 5/1990 | Rayhack ...................... 606/53 |
| 5,540,696 A | * | 7/1996 | Booth et al. ................... 606/88 |
| 5,776,197 A | * | 7/1998 | Rabbe et al. ............. 623/17.15 |
| 5,899,901 A | | 5/1999 | Middleton |
| 6,017,342 A | * | 1/2000 | Rinner ......................... 606/57 |
| 6,126,660 A | | 10/2000 | Dietz |
| 6,304,414 B1 | * | 10/2001 | Crue et al. ................... 360/126 |
| 6,328,738 B1 | * | 12/2001 | Suddaby ....................... 606/57 |
| 6,332,887 B1 | * | 12/2001 | Knox ............................ 606/87 |
| 6,340,363 B1 | * | 1/2002 | Bolger et al. .................. 606/90 |
| 6,416,528 B1 | * | 7/2002 | Michelson .................... 606/185 |

OTHER PUBLICATIONS

Website printout of EBI, L.P. (5 pages).
Website printout of DePuy AcroMed, Inc. (7 pages).
Website printout of Encore (3 pages).
Website printout of AAK E–Aesculap (3 pages).
Website printout of Cerfix (2 pages).
Website printout of Spinal Concepts, Inc. (3 pages).
Website printout of Interpore (6 pages).
Website printout of Mathys (5 pages).
Website printout of Sintea Biotech (2 pages).
Website printout of Endius (2 pages).
Website printout of Blackstone Medical (9 pages).

* cited by examiner

Primary Examiner—Pedro Philogene
Assistant Examiner—David A. Bonderer
(74) Attorney, Agent, or Firm—Weintraub Genshlea Chediak Sproul; John P. Costello

(57) ABSTRACT

The invention provides a fusion plate system, and method for installing this system upon a patient's spine. The system uses a distractor device which measures an appropriately sized fusion plate for a corpectomy or discectomy application. Once a properly sized fusion plate is selected, the distractor device compresses the vertebrae and any associated bone graft placed between the vertebrae, thereby assuring maximum contact between the vertebrae and bone graft at a corpectomy or discectomy location. Compression is maintained by the distractor device while the fusion plate is anchored upon the corpectomy or discectomy site. Furthermore, the inventive fusion plate system and method results in the fusion plate being properly centered upon a patient's spine, so that an aesthetically pleasing, as well as functional, surgical result is achieved.

17 Claims, 7 Drawing Sheets

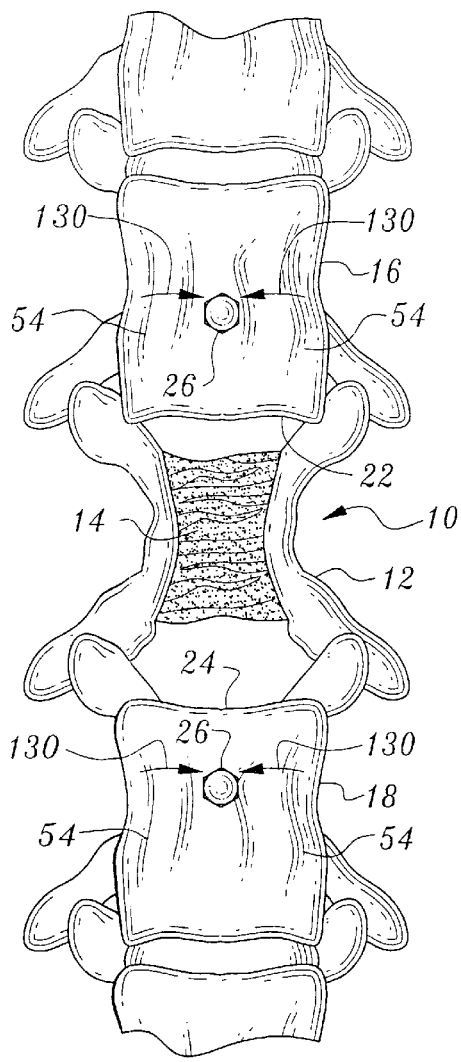
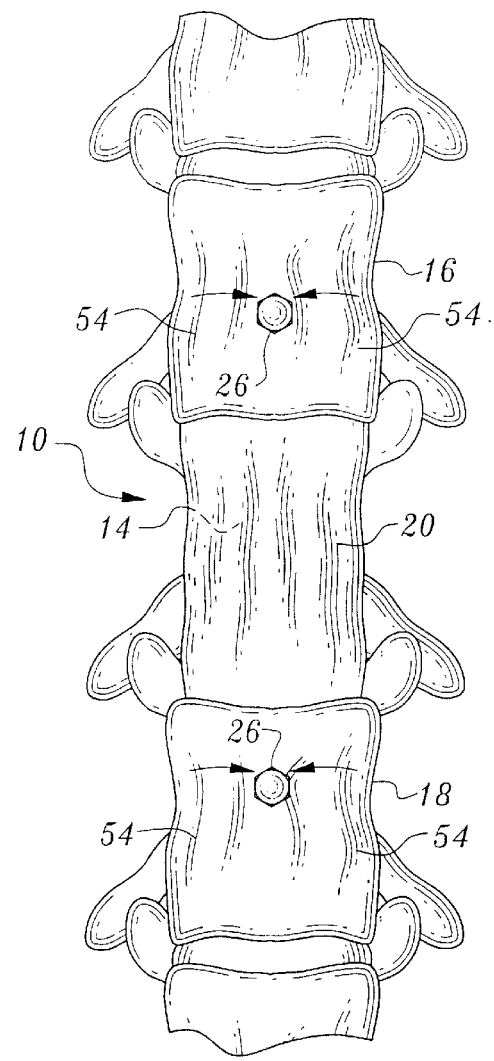
Fig. 1
Fig. 2
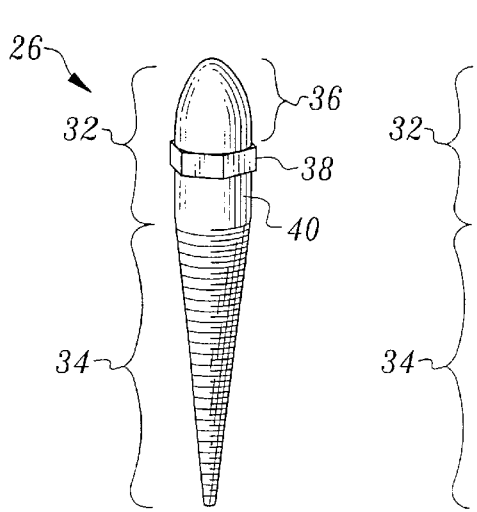
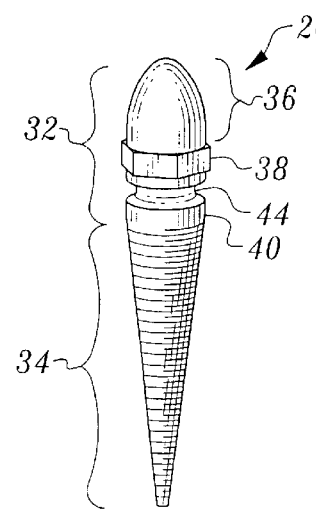
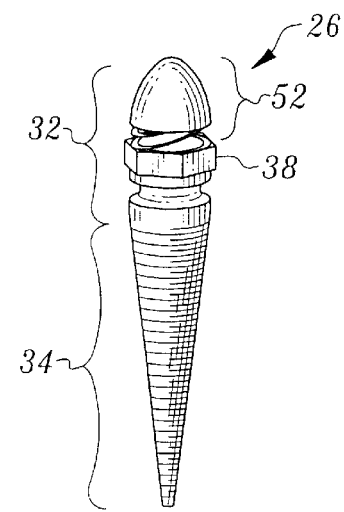
Fig. 3A   Fig. 3B   Fig. 3C

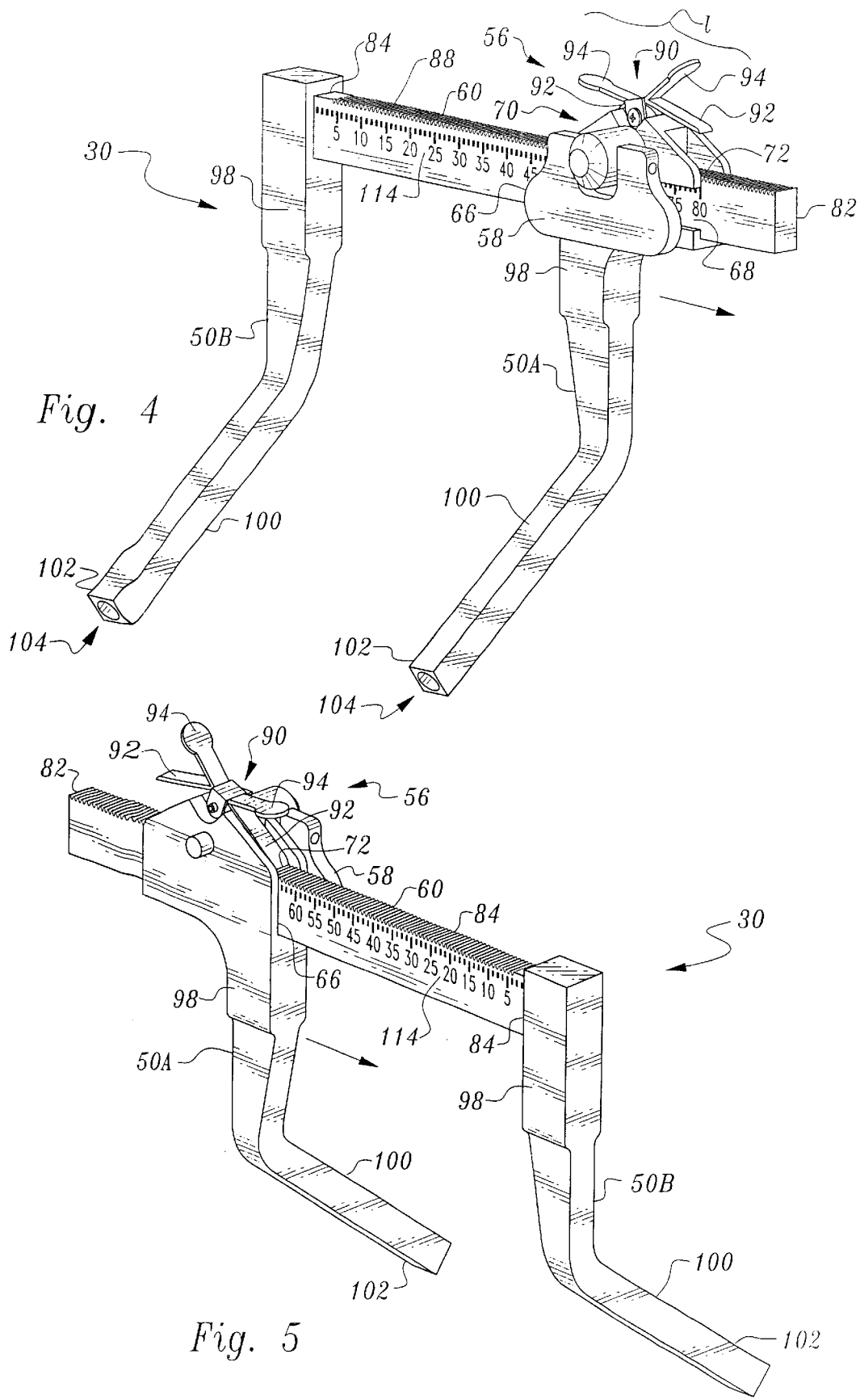

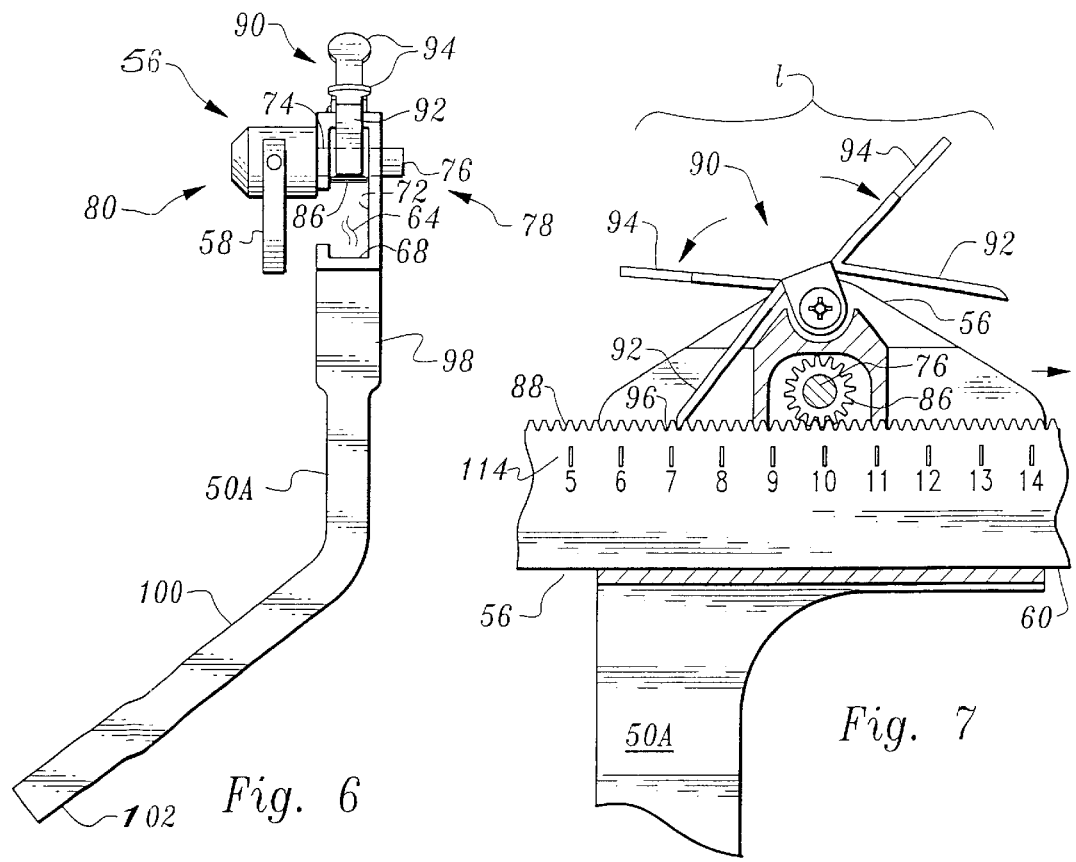
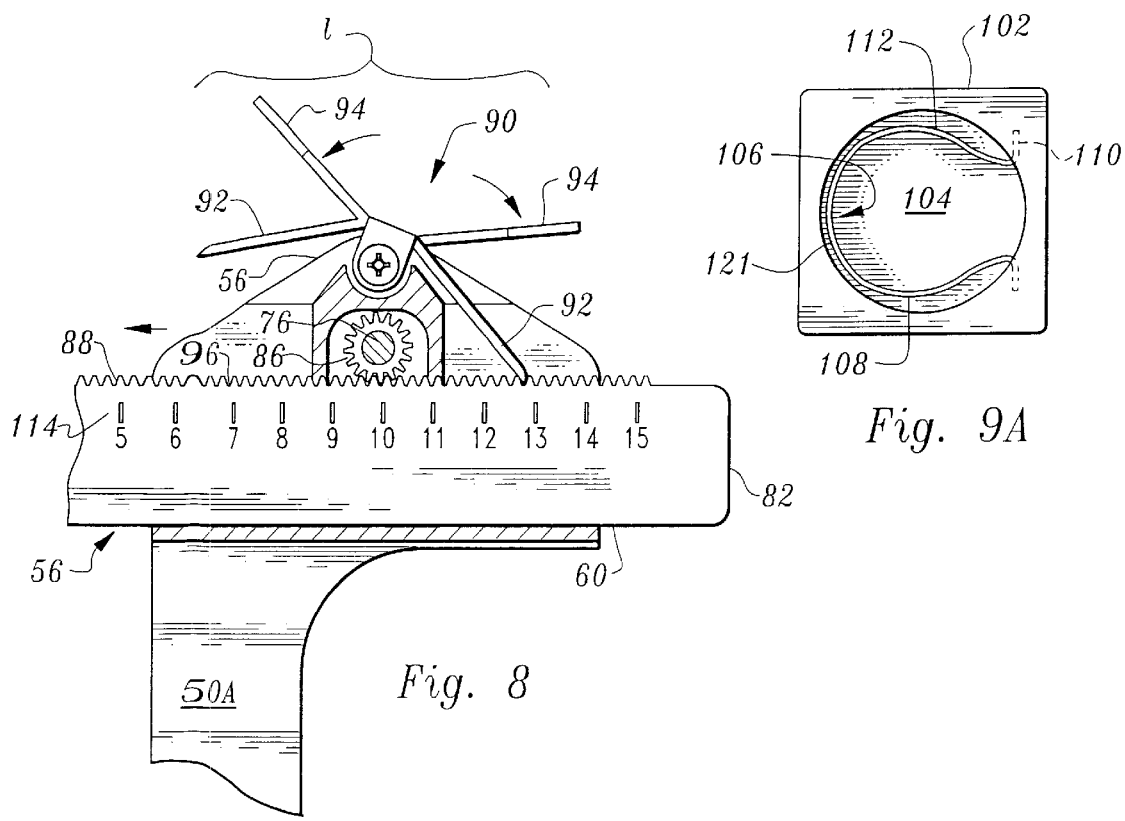

SYSTEM AND METHOD FOR FUSING SPINAL VERTEBRAE

TECHNICAL FIELD

This invention relates to appliances used in the stabilization and fusion of spinal vertebrae during and after spine surgery, and more specifically, relates to systems and methods for using a fusion plate for stabilizing vertebrae as part of a corpectomy or discectomy procedure to allow bone growth to occur.

BACKGROUND

Fusion plates have been in use as appliances for immobilizing and fusing adjacent spinal vertebrae following a discectomy (spinal disc removal) or for immobilizing the area surrounding a corpectomy (removal of an entire vertebral body). When these procedures are performed, a gap in the spine remains from the removed disc or vertebral body; this gap typically being closed by inserting a bone graft, usually from a cadaver. The adjacent vertebrae surrounding the discectomy or corpectomy site are then immobilized by attaching a fusion plate, usually on the anterior side of the spine, so that the vertebrae fuse to the bone graft, forming an entire fused section of the spine. Such fusing of vertebrae to the bone graft requires that the vertebrae remain immobile. Any movement during the healing process can cause a lack of fusion to occur, essentially forming a false joint in the spine at the discetomy or corpectomy site.

Presently, in performing a discectomy or corpectomy, a device called a "distractor" is used to spread the adjacent vertebrae so that the disc or vertebral body of interest can be removed. In use, a pair of distractor pins, which are essentially screws having a head for engaging with the distractor, are screwed into the vertebrae adjacent to the discectomy or corpectomy site. One pin is placed in the upper vertebra, and a second pin is placed in the lower vertebra, both vertebrae being directly adjacent to the discectomy or corpectomy site. The distractor tool is then coupled to the pins on the upper and lower vertebrae, above and below the site, and the vertebrae are then mechanically spread apart, for aiding in the removal of any remaining portion of the deteriorated disc or vertebral body, and also to create a gap for placing a bone graft. Once the bone graft is placed, the distractor is removed; next, the distractor pins are removed from the spine, and finally, a fusion plate is placed in a position for keeping the adjacent upper and lower vertebrae as well as the bone graft immobilized. The plate is screwed into the upper and lower vertebrae the goal of which is to provide sufficient immobility to cause fusion between the vertebrae and bone graft to occur. Examples of fusion plates presently existing in the art, which are used in the heretofore described manner, are those produced by EBI Biomet, Inc., Dupuy AcroMed, Inc., and Spinal Concepts, Inc, to name a few.

Two drawbacks with the present fusion plate methods and systems are: 1) the plate is often positioned off-center on the spine, during these procedures, due to the fact that there has not been a system in place to properly align the fusion plate on the spine; and 2) the above methods rely only on the natural compression of the spine (e.g. once the distractor is removed), to compress the vertebrae sufficiently against the bone graft, to allow fusion to begin. With regard to the first drawback, a fusion plate positioned off-center can result in aesthetic objections from a patient in whom a fusion plate has been implanted. This often occurs when a patient examines his spinal X-ray following surgery and the fusion plate is off-center, or crooked, leading the patient to surmise that the surgeon has performed a haphazard job. With regard to the second drawback, the failure to sufficiently compress the vertebra and bone graft together, prior to placing and anchoring the fusion plate, results in unnecessary space remaining between these components, and reduces the likelihood that fusion will occur (this can cause the "false jointing" problems noted above).

Therefore, a need exists for a fusion plate system and method which allows a section of spine to be compressed adequately following a corpectomy or discectomy, so that sufficient immobilization and spinal fusion can occur. Additionally, a need exists for a fusion plate system and method which allows a fusion plate to be centered properly upon a spine.

The foregoing reflects the state of the art of which the inventor is aware, and is tendered with a view toward discharging the inventors' acknowledged duty of candor, which may be pertinent to the patentability of the present invention. It is respectfully stipulated, however, that the foregoing discussion does not teach or render obvious, singly or when considered in combination, the inventor's claimed invention.

SUMMARY OF THE INVENTION

The invention overcomes the drawbacks of the prior art by providing a modified fusion plate system, and method for installing this system upon a patient's spine. This method and system allows a desired level of compression to be applied to the adjacent vertebrae surrounding the site of a corpectomy or discectomy, prior to, and during, the anchoring of the fusion plate. Furthermore, the inventive fusion plate system and method results in the fusion plate being properly centered upon a patient's spine, so that an aesthetically pleasing, as well as functional, surgical result is achieved.

The inventive system and method relies upon mechanically compressing the spine to draw vertebrae together until these vertebrae are in contact with a bone graft located in the gap left by a corpectomy or discectomy. Once the spine is compressed, the fusion plate is guided to a centered positioning upon the spine over the site of the corpectomy. Finally, the fusion plate is anchored upon the spine, while the spine is still undergoing mechanical compression. The reliance of this system and method upon mechanical compression of the spine while the fusion plate is anchored, is intended to reduce spaces between the bone graft and adjacent vertebrae at the site of a corpectomy or discectomy, as much as possible, so that spinal fusion has the greatest chance of occurring.

In the preferred embodiment, the inventive system uses a distractor device to not only distract (e.g. spread) vertebrae, in the manner presently used, but additionally, to mechanically compress vertebrae and any bone graft located there between. Furthermore, the addition of sizing graduations to the inventive distractor device, correlating to the sizes of different fusion plates, allows a properly sized fusion plate to be selected by the surgeon for a particular application, with minimal trial and error.

The inventive system and method uses distractor pins to properly guide the fusion plate to a centered positioning upon a patient's spine. Once guided onto the spine, the fusion plate is anchored with bone screws. The distractor pins are centered on the spine using anatomical landmarks such as the longis colli muscles or uncinate processes. The distractor pins are also designed for having a compressing force applied to them by the distractor device such that they do not bend or disengage from the distractor device upon compressing the spine to a desired level.

Accordingly, the following objects and advantages of the invention apply:

It is an object of this invention to provide a fusion plate system and method which results in improved fusion of spinal vertebrae following a corpectomy or discectomy.

It is another object of this invention to provide a fusion plate system and method which causes a fusion plate to be centered upon a patient's spine.

Further objects and advantages of the invention will be brought out in the following portions of the specification, wherein the detailed description is for the purpose of fully disclosing preferred embodiments of the invention, without placing limitations thereon.

BRIEF DESCRIPTION OF THE DRAWINGS

The invention will be more fully understood by reference to the following drawings which are for illustrative purposes only:

FIG. 1 is a plan view of the C-4 and C-6 vertebrae with the C-5 vertebral body removed as in a corpectomy procedure and wherein the C-4 and C-6 vertebrae each have a centered distractor pin coupled thereto.

FIG. 2 is a plan view of the C-4 and C-6 vertebrae shown with a bone graft positioned in the gap left by the removal of the C-5 vertebral body, this view again showing centered distractor pins coupled to the C-4 and C-6 vertebrae.

FIG. 3A is a perspective view of a first preferred embodiment of the distractor pin of the inventive system, this embodiment having a slender head portion and a section that is hexagonal for mating with a surgical wrench.

FIG. 3B is a perspective view of a second preferred embodiment of the distractor pin of the inventive system, this embodiment having a groove located at the bottom end of the pin head portion, this groove for mating with the terminal end of a distractor device armature.

FIG. 3C is a perspective view of a third preferred embodiment of the distractor pin having a spring loaded, flexible portion.

FIG. 4 is a perspective view of a distractor device of the inventive system, this view showing the carriage body and associated armature traveling in an extended (distracted) direction.

FIG. 5 is a perspective view of the distractor device of FIG. 4, showing the opposite side of the distractor device shown in FIG. 4, with the carriage body and associated armature traveling in a compressed direction.

FIG. 6 is an end view of the carriage body of the distractor device.

FIG. 7 is a closeup side cutaway view of the carriage body element positioned on a section of the rack of the inventive distractor device showing a two-way toggling mechanism toggling in a position for distraction.

FIG. 8 is a closeup side cutaway view of the carriage body element positioned on a section of the rack of the inventive distractor device showing a two-way toggling mechanism toggling in a position for compression.

FIG. 9A is a closeup view of a distractor device armature and the bore of its terminal end portion showing a spring clamp coupling mechanism for coupling to the head portions of distractor pins of the type shown in FIG. 3B.

FIG. 16 is an elevated perspective view of the distractor device of FIG. 4 coupled to distractor pins and compressing the C-4 and C-6 vertebrae against the bone graft while a fusion plate is positioned in a centered manner by distractor pins at the corpectomy site.

FIG. 17 is a closeup elevated perspective view of the terminal ends of the distractor device of FIG. 4 coupled to distractor pins and compressively holding the C-4 and C-6 vertebrae against the bone graft while a fusion plate is being anchored into place over the corpectomy site. Here a modified drill guide is used to apply the anchor screw to the fusion plate, the guide tube of drill guide being shown in cutaway with an anchor screw and screw driver placed therein. The terminal end of drill guide tube is shown seated in a chamfered region surrounding anchor holes

DESCRIPTION OF THE PREFERRED EMBODIMENTS

Figure 9B:
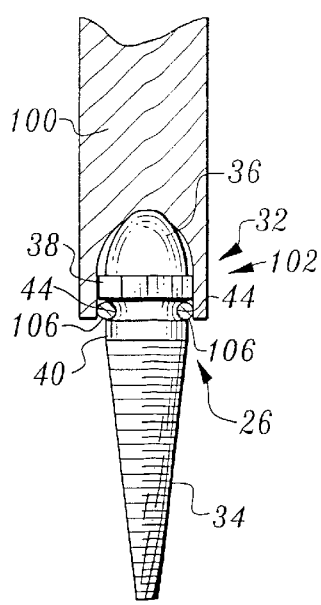
FIG. 9B is a closeup cutaway view of the terminal end portion of the inventive distractor device showing the spring clamp coupling mechanism engaging the head portion of a distractor pin of the type shown in FIG. 3B.

FIG. 1 illustrates a section of cervical spine 10 with a vertebral body (not shown) removed from a fifth cervical vertebrae (C-5) 12 as would result in a standard corpectomy procedure. While the cervical section of a human spine is shown here, this is for illustrative purposes only, as this invention could be used on other vertebral sections, such as the thoracic or lumbar sections of the spine. Additionally, while a human spine is shown in the drawings, the inventive system and method could be adapted to be used on sections of animal spines. In surgery the vertebral body of the (C-5) 12 vertebrae would have been removed in sections, being careful not to damage the dura covering (not shown) of the spinal cord, thereby leaving a gap 14 having the fourth (C-4) 16 and sixth (C-6) 18 cervical vertebrae located adjacent to gap 14.

In a corpectomy procedure the gap 14 is filled with a bone graft 20 that is sized and shaped to fill gap 14 snugly as is shown in FIG. 2. Prior to placing a bone graft into gap, the bottom surface 22 of the C-4 vertebrae and the top surface 24 of the C-6 vertebrae are usually scored by the surgeon to cause bleeding. This blood flow encourages the ossification process to occur between the cervical vertebrae 16, 18 and the bone graft 20 placed in gap 14, thereby causing fusion of these elements. If gravity is the only force acting on the spine to draw vertebrae 16, 18 in contact with the bone graft 20, it is possible for enough space to remain between the contacting surfaces of these elements, such that fusion will not occur at all. If fusion does not occur, this may necessitate a second surgery to correct the problem.

As shown in FIGS. 1 and 2, first and second distractor pins 26 are placed in the (C-4) 16 and (C-6) 18 vertebrae. In the inventive method and system, distractor pins 26 are used as leverage points for the application of a distractor device 30 for purposes of both distracting, or spreading, the vertebrae, and additionally, for compressing the vertebrae. Due to the application of compressive force by the inventive method and distractor device, it is preferred that distractor pins 26, be constructed from a non-bendable material such as titanium alloy.

FIG. 3A illustrates a distractor pin 26 of a preferred shape to accomplish the inventive system and method. Distractor pin 26 has a head portion 32 for coupling to a distractor device and a screw portion 34 for attaching to vertebrae. Preferably, head portion 32 is tapered 36 at its top with an overall slender cylindrical profile below the tapered top having a substantially uniform cylindrical diameter. A small hexagonal section 38 for engaging with a surgical wrench aids in driving the distractor pin into the vertebra. Alternately, the head portion 32 can also be designed to be a phillips head, for example, or designed with another means for driving screw portion 34 into vertebrae. The lower section 40 of head portion 32 is cylindrical with the rest of the head portion for engaging with the fusion plate 42 in a manner described further below.

FIG. 3B illustrates a second embodiment of distractor pin 26 with head portion 32 having a groove 44 located above lower section 40. This groove 44 mates with a spring clamp 106 located in the bore 104 of the armature 50A, 50B of distractor device 30 to form a coupling mechanism as further described below.

FIG. 3C illustrates a third embodiment of distractor pin 26 having a spring loaded, flexible top 52. The flexible top allows a surgeon to bend the top 52 slightly into the bore 104 of the armature 50A, 50B of the distractor device 30, thus serving as a bore-guide. Flexible top 52 is especially useful in the bloody conditions of surgery where guiding the distractor armature 50A, 50B onto the head portion 32 of the distractor pin 26 is often done by feel. Distractor pins 26 are preferably approximately 12–14 mm long, with the screw portion 34 comprising the majority of the length of the distractor pin in relation to the head portion 32. The screw portion 34 can be altered in length to conform to a range of patient's bone depth and density. For example, an osteoporotic patient may require a screw portion 34 longer than normal to allow additional purchase of the distractor pin 26 in the deteriorating bone.

Referring again to FIGS. 1 and 2, the step in the inventive method of centering distractor pins 26 can be examined. The method described here for centering distractor pins 26 on the (C-4) and (C-6) 16, 18 vertebrae shown here would apply to other vertebrae located at other sections of the spine as well. The preferred method for accomplishing this step involves choosing a bilaterally symmetrical anatomical landmark such as the longis colli muscles (not shown), or the uncinate processes 54 of the vertebrae and using these landmarks for centering the distractor pins 26. These landmarks are typically equidistant from the center of the cervical vertebra, and hence, the surgeon needs only to confirm the location of the equidistant center (demonstrated hereby arrows 130) and attach a distractor pin 26 to the vertebrae at that location, as shown in FIGS. 1 and 2.

Upon placing the distractor pins 26 in the manner heretofore described, a distractor device 30, the preferred embodiment of which is shown in FIGS. 4 and 5 is coupled to distractor pins 26. As shown, distractor device 30 is comprised of a carriage body 56, a first armature 50A coupled to carriage body 56, a rack 60 for allowing the carriage body 56 a range of motion and a second armature 50B coupled at an end of the rack 60.

Referring also to FIGS. 6 and 7 carriage body 56 defines a chamber 64 along its length l. Chamber 64 has first and second openings 66, 68 at an engagement end 70 and the opposite end 72 respectively, and openings 66, 68 are in communication with the chamber 64. The body 56 also defines a gear bore 74 at a location along length l, the gear bore 74 being in communication with chamber 64. Gear bore 74 has an axis 76 which is perpendicular to length l of chamber. Gear bore 74 is preferably defined through carriage body 56 from the first side 78 to the opposite side 80 of the body 56.

Referring again to FIGS. 4 and 5 and still to FIGS. 6 and 7, rack 60 is slidably disposed through first opening 66 and within the chamber 64. Rack 60 has a first end 82 for engaging with first opening 66 and a second end 84 having a second armature 50B coupled thereto. Rack 60 is slidable between a number of extended and compressed positions. FIG. 4 shows device 30 having rack 60 extended while FIG. 5 shows device 30 with rack being compressed to draw armatures 50A, 50B together. Rack 60 moves between extended and compressed positionings by engaging with gear 86 in gear bore 74, using a number of spaced apart teeth 88 located on rack 60.

Referring still to FIG. 7 and now to FIG. 8 the distractor device 30 also includes a two-way toggle switch 90 located atop carriage body 56, toggle switch for allowing first armature 50A coupled to carriage body 56 to alternately travel closer to, or away from, second armature 50B. Carriage body 56 and its associated armature 50A when traveling further from second armature 50B causes distraction, or spreading of the vertebrae. Alternatively travel of carriage body 56 closer to second armature 50B causes compression of vertebrae. Depending on the direction of travel desired, toggle switch 90 is switched so that the engaging member 92 located at each end of toggle switch arm 94 engages the gear teeth 88 of rack 60. FIG. 7 shows the actuation position of toggle switch for distraction, while FIG. 8 shows the proper actuation position of toggle switch for compression. Upon switching toggle switch to a desired direction, engaging member is biased against gear teeth 88 by a spring (not shown), so that as handle 58 is turned, engaging member 92 is dragged over gear teeth 88 and locks in the valley of gear teeth. Upon locking, engaging member 92 prevents carriage body 56 from traveling in the opposite undesired direction, from which toggle switch 90 has been actuated.

Referring now to FIGS. 9A and 9B and still to the previous figures, the armatures 50A, 50B of distractor device 30 can be examined. First armature 50A coupled to carriage body 56 is comprised of a first section 98 extending substantially perpendicularly outward from carriage body 56 and a second section 100 bent at an obtuse angle in relation to first section. Second armature 50B is comprised of two similar sections 98, 100 as first armature 50A, except that second armature is stationarilly engaged to the end 84 of rack. FIG. 9A is a closeup of the terminal end 102 of either first or second armature 50A, 50B showing a bore 104 axially disposed within second section 100 of armature, the bore preferably including a coupling mechanism comprised of a spring clamp 106 for receiving and releasably holding the head portion 32 of a distractor pin 26 therein. Spring clamp 106 is preferably horseshoe-shaped with the semicircular portion 108 having a slightly smaller diameter than the head portion of distractor pin 26 of the type shown in FIG. 3B. The ends 110 of the horseshoe shape of spring clamp 106 are flexibly anchored to the body of terminal end 102. The top 36 of distractor pin 26 is preferably tapered, as previously discussed, to easily slide spring clamp 106 over and onto the head portion 32. As shown in FIG. 9B, upon positioning around head portion 32, spring wire expands into space 121 inside of bore 104 and then compresses upon reaching groove 44 of distractor pin 26. Once inside groove 44, spring clamp 106 prevents distractor device 30 from migrating upward and slipping off of distractor pins 26 while vertebrae are being compressed. Spring clamp 106 can be removed from distractor pins 26 by applying gentle upward pressure on armatures 50A, 50B until device 30 disengages from distractor pin 26.

Figure 10A:
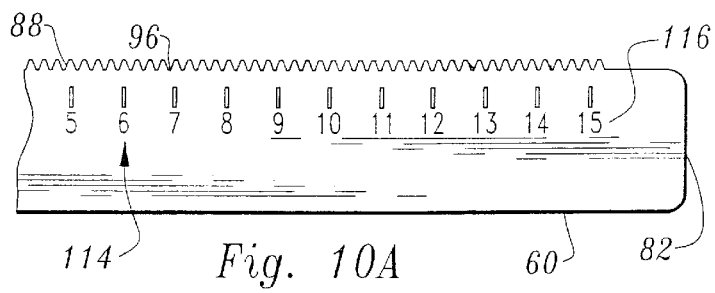
FIG. 10A is a closeup view of a section of the rack portion of the inventive distractor device having a measuring scale graduated in millimeters.
Figure 10B:
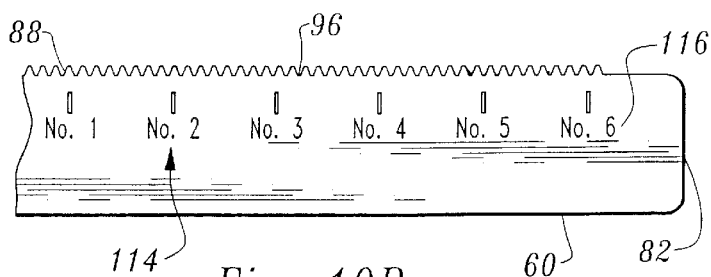
FIG. 10B is a closeup view of a section of the rack portion of the inventive distractor device having a measuring scale indicating an exemplary manufacturer's fusion plate model numbers.

Referring now to FIGS. 10A and 10B distractor device 30 includes a measuring scale 114 located upon rack 60 which allows a surgeon to select a properly sized fusion plate 42 for attachment at the site of a corpectomy or discectomy. Measuring scale 114 corresponds to a distance between the terminal ends 102 of armatures 50A, 50B, this distance corresponding to a preferred fusion plate size which will most likely fit over the site of a corpectomy or discectomy. Measuring scale 114 may have standard indicia 116, such as millimeters or inches as shown in FIG. 10A, or else correspond to a particular sizing convention associated with a particular manufacturer for the plurality of fusion plates it produces, as shown in FIG. 10B. For example a manufacturer may designate a plate as a "No. 1 plate" a "No. 2 plate" etc., to designate different sizes. Measuring scale 114 ensures that a properly fitted plate 42 will be placed by the surgeon with minimal trial and error.

Figure 11A:
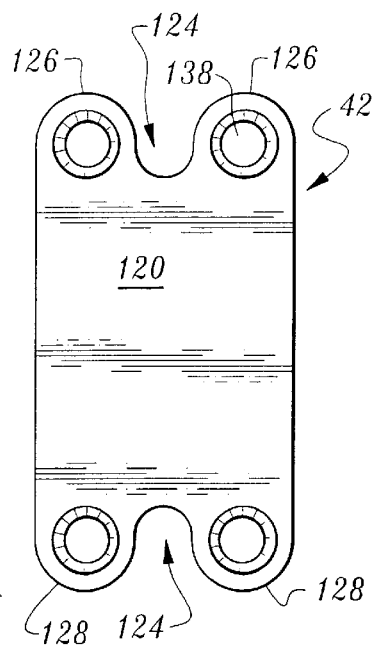
FIG. 11A is a plan view of a fusion plate used for a discectomy procedure, having a cleft engagement means for snugly engaging the head of a distractor pin.
Figure 11C:
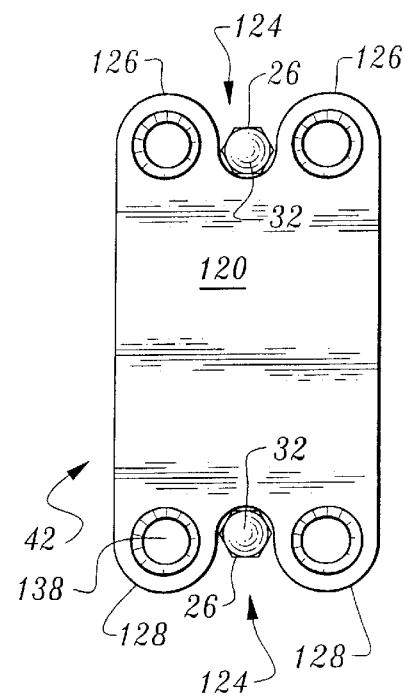
FIG. 11C is a plan view of the fusion plate shown in FIG. 11A showing the head portions of distractor pins snugly engaged within the cleft engagement means of the fusion plate.
Figure 11B:
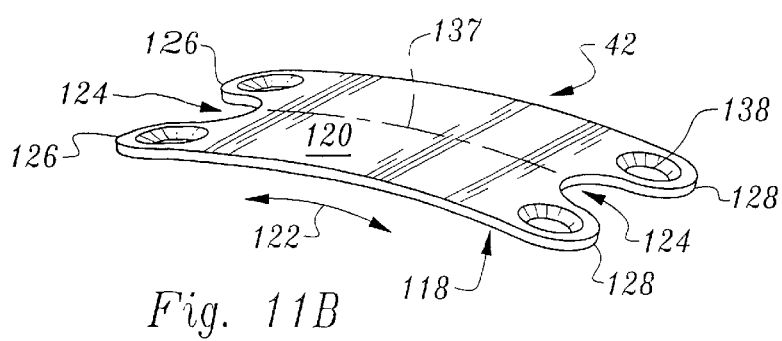
FIG. 11B is a perspective view of the plate shown in FIG. 11A showing the plate having a curvature for conforming to the shape of the anterior portion of a spine.
Figure 12A:
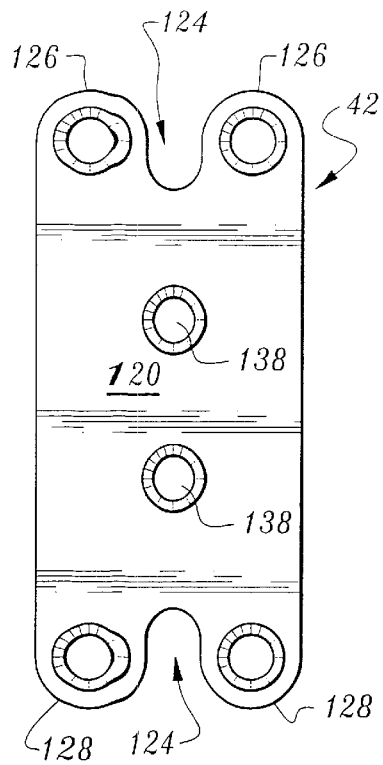
FIG. 12A is a plan view of a fusion plate used for a corpectomy procedure.
Figure 12C:
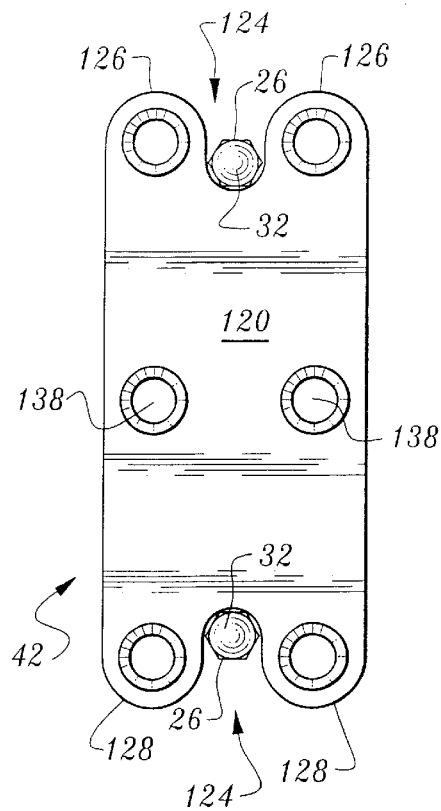
FIG. 12C is a plan view of the fusion plate shown in FIG. 12B showing the head portions of distractor pins snugly engaged within the cleft portions of the plate.
Figure 12B:
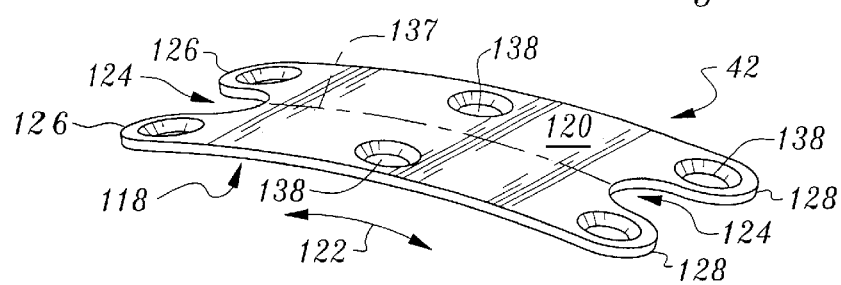
FIG. 12B is a perspective view of another style of fusion plate used for a corpectomy procedure this view showing a curvature for conforming to the shape of the anterior portion of a spine.

FIGS. 11A–C and 12A–C illustrate exemplary fusion plates 42 which comprise the inventive system and method. Fusion plates 42 are preferably surgical quality metal, such as titanium alloy, but composite materials which are not rejected by the immune response of the human body could also be used. Additionally, fusion plates may be comprised of a synthetic absorbable material which dissolves over time. Fusion plates 42 shown here, are for cervical applications and are fashioned to be placed upon the anterior portion of the cervical spine 10. In FIGS. 11A–C fusion plate 42 is shorter and designed for use at the site of a discectomy. In FIGS. 12A–C fusion plate 42 is elongate for purposes of spanning the site of a corpectomy. The size of a bone graft required to fill in the site of a corpectomy is greater than the size of a bone graft required to fill in a discectomy, hence the differences in the length of fusion plates adapted to each separate procedure.

Fusion plate 42 has an inner surface 118 and an outer surface 120, inner surface for contacting the anterior portion of the cervical spine 10. Inner surface 118 preferably has at least a slight curvature 122 along its longitudinal axis for conforming to a similar curvature of the section of spine to which the fusion plate 42 will attach. For cervical applications the inner surface 118 has a slight concave curvature 122 along its longitudinal axis of the plate 42. The plate can be bent further by the surgeon if needed. The inventive system and method requires that fusion plate 42 engage distractor pins 26 for purposes of centering fusion plate 42 properly. As shown in FIGS. 11A–C and 12 A–C, cleft 124 at upper 126 and lower 128 edges located centrally along the longitudinal axis of fusion plate 42 has a width for engaging snugly with lower section 40, of the distractor pin head portions 32.

Figure 13:
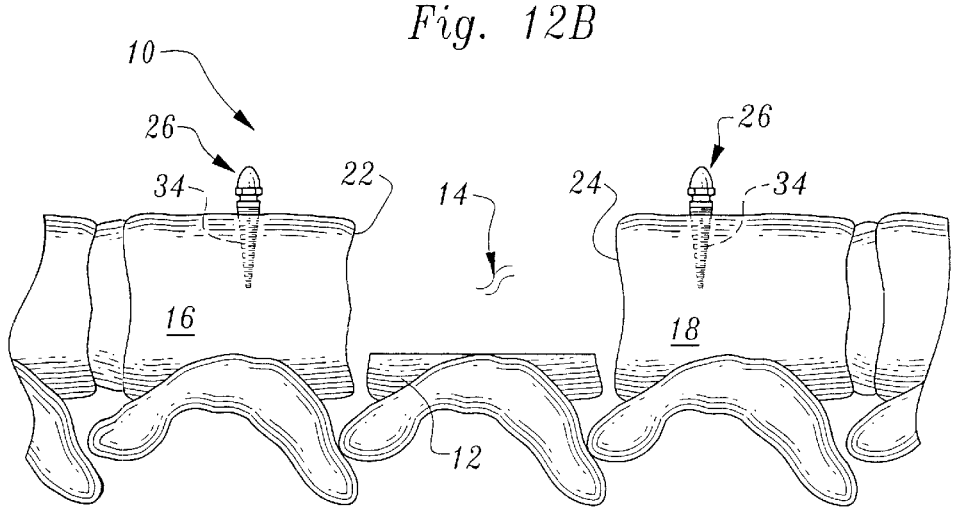
FIG. 13 is a side view of the C-4 and C-6 vertebrae with the C-5 vertebral body removed and a gap located there between, as would occur in a corpectomy procedure. The distractor pins are aligned perpendicularly to the C-4 and C-6 vertebrae.

Referring again to FIGS. 1 and 2 and additionally to FIG. 13 the remainder of the inventive surgical method can be described. Prior to placing distractor pins 26 in the centered manner as previously described, a determination of bone depth and density must be performed. This can be accomplished by taking an intra-operative lateral spine x-ray. The bone depth and denisty of the vertebrae must be sufficient to anchor distractor pins 26 and bone screws.

Once the central location on the vertebrae is determined, the surgeon preferably positions distractor pins 26 using an alignment guide (not shown) of a type well known in the art to make sure that distractor pins are perpendicular upon the spine, as shown in FIG. 13. Perpendicular placement of the distractor pins 26, aids in properly engaging terminal ends 102 of the armatures 50A, 50B of distractor device 30. Once aligned, distractor pins 26 are then driven into the vertebrae at the centered locations using a hexagonal surgical wrench (not shown), until the screw portion 34 of the distractor pins 26 are seated within the vertebra, at a sufficient depth for allowing compression by the distractor tool 30 to occur.

Figure 14:
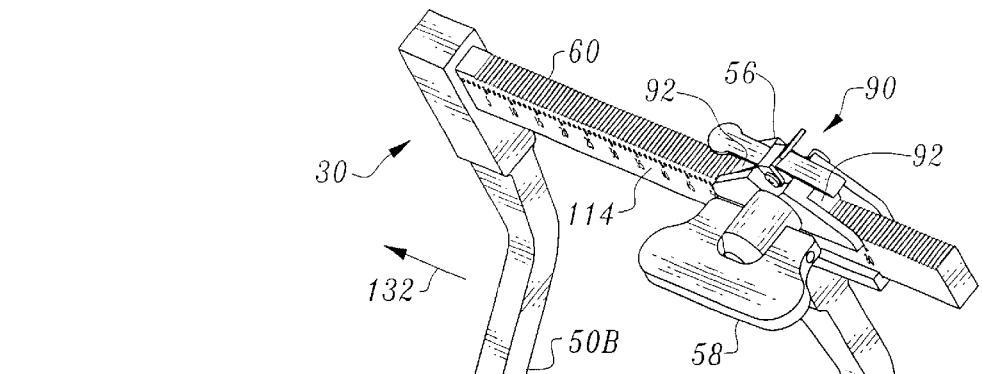
FIG. 14 is an elevated perspective view of the distractor device of FIG. 4 coupling to distractor pins in turn coupled to the C-4 and C-6 vertebrae and spreading these vertebrae apart. The C-5 vertebral body has been removed as in a corpectomy procedure and a bone graft has been placed in the gap left by the removal of the vertebral body. The spreading of the vertebrae here allows the vertebral body to be removed from the C-5 vertebrae and allows the bone graft to be placed.

Next, as shown in FIG. 14, terminal ends 102 of distractor device 30 are attached to the heads 32 of distractor pins 26. A coupling mechanism 106 of the type previously noted in FIGS. 9A and 9B engages and couples onto groove 44 of head portions 32. The toggle switch 90 on the carriage body 56 is actuated for spreading the (C-4) and (C-6) vertebrae 16, 18 and handle 58 is turned to spread these vertebrae in the direction 132 shown. Next, the vertebral body (not shown) of the C-5 vertebrae 12 is removed. The engaging member 92 locks distractor 30 in a spread position, at this point, in preparation for placing a bone graft 20 between the (C-4) and (C-6) vertebrae 16, 18. The bottom surface 22 of the (C-4) vertebrae and top surface 24 of the (C-6) vertebrae are cleaned and scored to promote blood flow. Next, a bone graft 20 of appropriate size and shape is placed in the gap 14 left by the removal of the (C-5) vertebral body.

Figure 15:
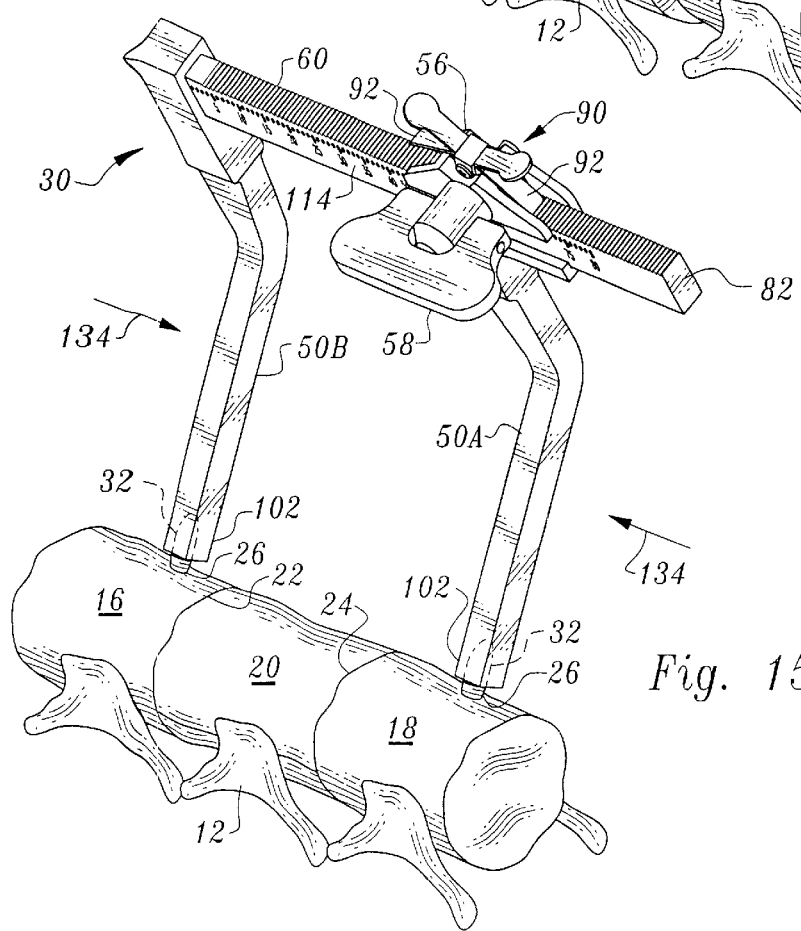
FIG. 15 is an elevated perspective view of the distractor device of FIG. 4 coupled to distractor pins in turn coupled to the C-4 and C-6 vertebrae with a bone graft filling the gap left by the removal of the C-5 vertebral body as in a corpectomy procedure. Here the distractor device is being used to compress the C-4 and C-6 vertebrae against the bone graft.
Figures 16, 17:
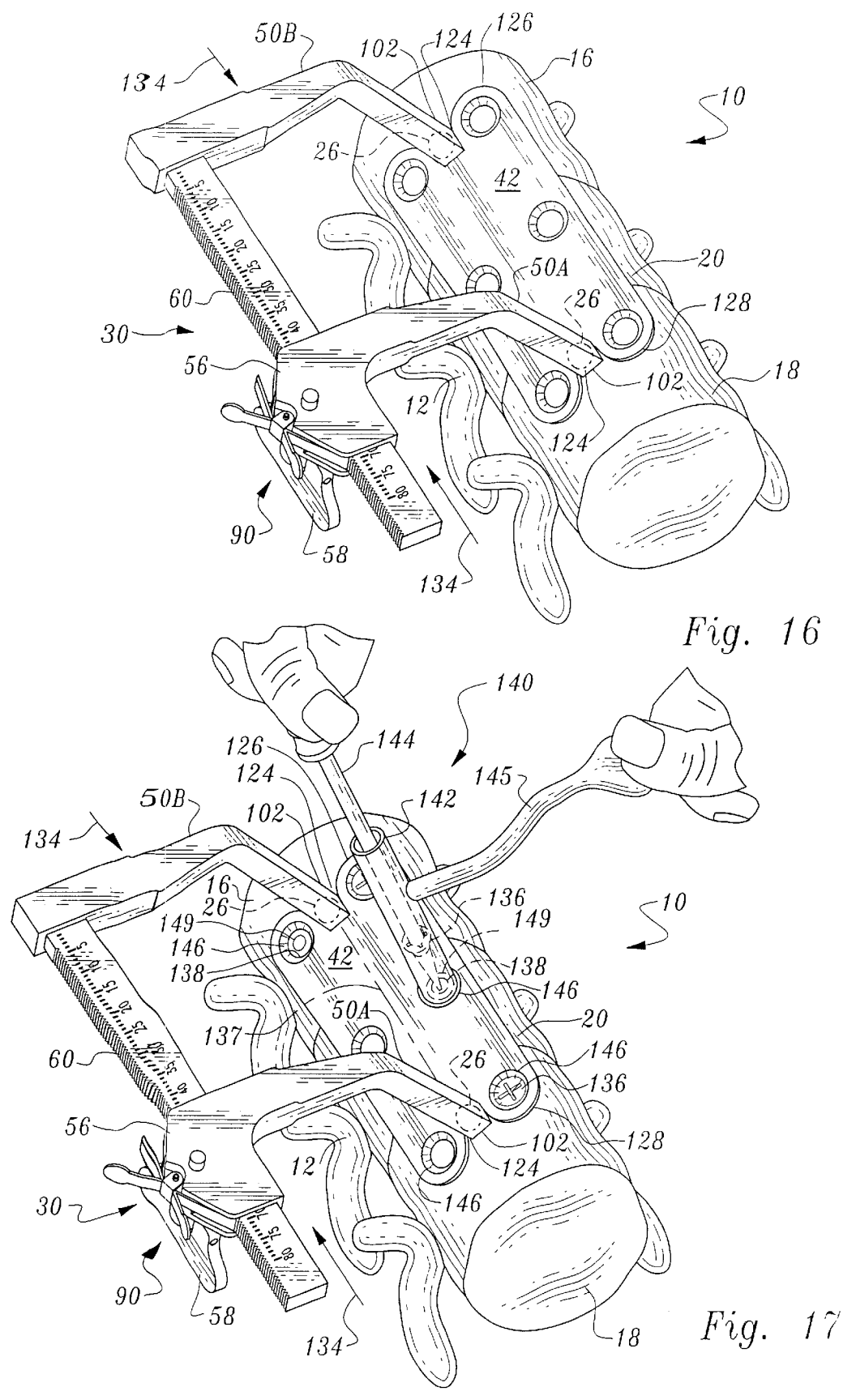

Referring to FIGS. 15 and 16 the steps of placing the fusion plate 42 and compressing the vertebrae using the mechanical compression exerted by the distractor device 30, are demonstrated. Distractor device 30 remains engaged upon the heads of distractor pins 26, and toggle switch 90 is actuated to cause carriage body 56 to travel in the direction 134 resulting in compression. Handle 58 is turned in a direction so as to compress the spine 10 until the (C-4) and (C-6) vertebrae 16, 18 contact the bone graft 20. Engagement member 92 locks first armature 50A at the desired level of compression and keeps it there, thereby maintaining compression upon the bone graft 20 by the adjacent vertebrae 16, 18. Once the desired level of compression is reached, the surgeon can then read the measuring scale 114 on the rack 60 of the distractor device 30 to determine the appropriately sized fusion plate 42 which should be used in a particular application. The cleft 124 located at each of the opposite ends 126, 128 of fusion plate 42 allows the surgeon to engage a properly sized fusion plate 42 upon the distractor pins 26 without removing the distractor device 30. The fusion plate engages lower section 40 of head portion with cleft 124. The clefts are preferably centered along the longitudinal axis of the fusion plate. This engagement results in the fusion plate 42 being centered upon the spine 10, at the area of the corpectomy. The maintenance of compression on the spine 10, while the fusion plate 42 is being placed, ensures that a minimal amount of space exists between the bone graft 20 and its adjacent vertebrae 16, 18, thereby providing the best chance for fusion to occur.

As further shown in FIG. 17, once compressed, bone screws 136 are placed in anchor holes 138 using a drill guide 140. Bone screws 136 may be comprised of titanium alloy, composite material or synthetic absorbable material. Anchor holes 138 are preferably placed exterior to the longitudinal axis 137 of the fusion plate 42. However, as shown in FIG. 12A anchor holes 138 may also be placed on the longitudinal axis, as some surgeons prefer to anchor fusion plate directly in the bone graft 20, as well as in the adjacent vertebrae 16, 18. Drill guides are commonly used in spinal surgery, however the drill guide 140 shown has a wider diameter guide tube 142 to allow for a drill bit to work therein to start a pilot hole in both the patient's vertebrae 16, 18 and bone graft 20. The wider diameter of guide tube 142 also allows enough space to drop a bone screw 136 down the guide tube 142 and drive it into the spine 10 with a screw driver 144. Alternately, guide tube 142 can be used to hold bone screw 136 upright and start driving bone screw into spine 10 without first drilling a pilot hole. By using a drill guide 140 to guide bone screws 136 without using a pilot hole, bone screws are added in one step, and the frequent struggle to find a pilot hole in the middle of surgery is eliminated. Drill guide 140 is held steady during the addition of bone screws 136 by handle 145. To further ensure the proper alignment of bone screws 136, a furrowed region 146 surrounding anchor hole 138 allows the terminal end 148 of guide tube 142 to seat in an aligned manner upon fusion plate 42. Additionally, anchor hole 138 includes chamfer 149 which allows bone screw 136 to seat flush with top surface 120 of fusion plate 42. Anchor holes 138 may include locking washers (not shown) seated therein to prevent bone screws 136 from backing out.

Clefts 124 at each of the opposite ends 126, 128 preferably do not protrude beyond anchor holes 138 located at each of ends 126, 128. Distractor pins 26 have been previously placed at a location on the vertebrae where bone density is adequate for strong implantation, to withstand the leveraging force on the distractor pins 26 due to compression. The region near the cleft 124, on average, has a similar sufficient bone density for placement of the bone screws 136. By positioning clefts 124 so that they do not protrude beyond anchor holes 138, an increased likelihood that bone screws 136 will be inserted into a similar region of adequate bone density as the distractor pins 26, occurs.

When the fusion plate 42 is fully anchored, the distractor device 30 and distractor pins 26 are removed from the patient's spine. When fusion plate 42 is anchored, bone graft 20 and its adjacent vertebrae 16, 18 are immobilized in a contacting manner, thereby creating the best conditions for bone fusion to occur.

The foregoing detailed disclosure of the inventive system and method is considered as only illustrative of the preferred embodiment of, and not a limitation upon the scope of, the invention. Those skilled in the art will envision many other possible variations of the system and method for its use as disclosed herein that nevertheless fall within the scope of the following claims. And, alternative uses for this system and method may later be realized. Accordingly, the scope of the invention should be determined with reference to the appended claims, and not by the examples which have herein been given.

I claim:

1. A system for promoting the fusion of vertebrae to a bone graft in a spinal column, the system comprising:

first and second distractor pins;

a fusion plate including engaging means for engaging paid first and second distractor pins;

a distractor device having distractor pin coupling means for coupling to said first and second distractor pins when said distractor pins are coupled protrudingly from a first and a second vertebrae;

said distractor device further comprising fusion plate measuring means;

said distractor device coupling to said first and second distractor pins with said pin coupling means and compressively drawing together a first and a second vertebrae coupled to said distractor pins until a desired level of compression against a bone graft is achieved; and anchoring means for anchoring said fusion plate to a first and a second vertebrae while maintaining a desired level of compression upon said distractor pins with said distractor device.

2. The system of claim 1, wherein said engaging means is centrally positioned along a longitudinal axis of said fusion plate.

3. The system of claim 2, wherein said fusion plate further comprises an inner surface conforming approximately to an anterior surface of a spinal column.

4. The system of claim 3, wherein said fusion plate further comprises anchoring holes located exterior to said longitudinal axis of said fusion plate.

5. The system of claim 4, wherein said anchoring means further comprises at least one bone screw, said anchoring holes for receiving said bone screw there through and anchoring said fusion plate to a first and a second vertebrae.

6. The system of claim 4, wherein said engaging means further comprises a first cleft located along an upper edge of said fusion plate and a second cleft located along a bottom edge of said fusion plate.

7. The system of claim 2, wherein said engaging means further comprises a first cleft located along an upper edge of said fusion plate and a second cleft located along a bottom edge of said fusion plate.

8. The system of claim 1, further comprising an alignment guide for aligning said distractor pins perpendicularly upon a first and a second vertebrae to which they are coupled.

9. The system of claim 1, wherein said distractor pins are comprised of titanium alloy.

10. The system of claim 9, wherein said distractor pins are 12–14 mm in length.

11. The system of claim 1, wherein said anchoring means further comprises anchor holes imparted through said fusion plate.

12. The system of claim 11, wherein said fusion plate further comprises locking washers located in said anchor holes.

13. The system of claim 12, wherein said anchoring means further comprises at least one bone screw, said anchor holes for receiving said bone screw there through, said washers serving to lock said bone screw and said fusion plate to a first and a second vertebrae.

14. A system for promoting the fusion of a section of spine, the system comprising:

a fusion plate;

compressing means for compressing a spine so that a first and a second vertebrae are drawn toward each other;

engaging means for engaging said fusion plate at a centered positioning upon a spine; and anchoring means for anchoring said fusion plate to a spine upon achieving a desired level of compression with said compressing means.

15. The system of claim 14, wherein said compressing means further comprises fusion plate measuring means.

16. The system of claim 14, wherein said engaging means engages said fusion plate at a longitudinally centered location upon a first and a second vertebrae.

17. A distractor device, comprising:

first means for disengageably coupling to first and second distractor pins respectively, anchored in a first and second vertebrae;

second means for compressing and distracting a first and a second vertebrae in relation to each other; and, third means for measuring the size of a fusion plate while said first and second means are maintained in a compressed position along with a first and a second vertebrae.

* * * * *